US010104331B2

(12) United States Patent
Amling et al.

(10) Patent No.: US 10,104,331 B2
(45) Date of Patent: Oct. 16, 2018

(54) CAMERA CONTROL UNIT WITH STEREOSCOPIC VIDEO RECORDING AND ARCHIVE

(71) Applicants: Marc R. Amling, Santa Barbara, CA (US); Timothy King, Goleta, CA (US); Grant deGoede, Solvang, CA (US); Lisa Blake, Santa Barbara, CA (US)

(72) Inventors: Marc R. Amling, Santa Barbara, CA (US); Timothy King, Goleta, CA (US); Grant deGoede, Solvang, CA (US); Lisa Blake, Santa Barbara, CA (US)

(73) Assignee: Karl Storz Imaging, Inc., Goleta, CA (US)

(*) Notice: Subject to any disclaimer, the term of this patent is extended or adjusted under 35 U.S.C. 154(b) by 219 days.

(21) Appl. No.: 14/836,239

(22) Filed: Aug. 26, 2015

(65) Prior Publication Data
US 2015/0366442 A1 Dec. 24, 2015

Related U.S. Application Data

(63) Continuation-in-part of application No. 13/731,395, filed on Dec. 31, 2012, now Pat. No. 9,841,280.

(51) Int. Cl.
*A62B 1/04* (2006.01)
*H04N 5/77* (2006.01)
(Continued)

(52) U.S. Cl.
CPC ............ *H04N 5/77* (2013.01); *A61B 1/0005* (2013.01); *A61B 1/00009* (2013.01); *A61B 1/00039* (2013.01); *A61B 1/00105* (2013.01); *A61B 1/00193* (2013.01); *A61B 1/04* (2013.01); *G01C 11/04* (2013.01); *H04N 9/8042* (2013.01); *H04N 13/0239* (2013.01); *H04N 13/239* (2018.05)

(58) Field of Classification Search
CPC .... H04N 5/77; H04N 13/0239; H04N 13/239; H04N 9/8042; G01C 11/04; A61B 1/00009; A61B 1/00039; A61B 1/0005; A61B 1/00105; A61B 1/04; A61B 1/00193
USPC .......................................................... 348/65
See application file for complete search history.

(56) References Cited

U.S. PATENT DOCUMENTS 6,960,161 B2 11/2005 Amling et al.
7,212,227 B2 5/2007 Amling et al.
(Continued)

OTHER PUBLICATIONS

U.S. Office Action U.S. Appl. No. 13/731,395 dated Jan. 9, 2017 14 pages.
(Continued)

*Primary Examiner* — Allen Wong
(74) *Attorney, Agent, or Firm* — Whitmyer IP Group LLC

(57) ABSTRACT

A video imaging system, and more particularly, a modular video imaging system having a control module connectable to multiple input modules. The input modules each capable of receiving differing types of image data from different types of cameras including stereoscopic camera configurations and processing the image data into a format recognizable by the control module. The control unit providing general functions such as user interface and general image processing that is not camera specific including the generation of a 3D image stream formed by combining two image streams.

22 Claims, 5 Drawing Sheets

(51) Int. Cl.
*H04N 13/02* (2006.01)
*H04N 13/239* (2018.01)
*A61B 1/00* (2006.01)
*A61B 1/04* (2006.01)
*G01C 11/04* (2006.01)
*H04N 9/804* (2006.01)

(56) References Cited

U.S. PATENT DOCUMENTS

| | | |
|---|---|---|
| 7,316,646 B2 | 1/2008 | Amling et al. |
| 7,471,310 B2 | 12/2008 | Amling et al. |
| 7,520,853 B2 * | 4/2009 | Amling ............. A61B 1/00059 348/207.11 |
| 7,821,530 B2 | 10/2010 | Amling et al. |
| 7,855,727 B2 | 12/2010 | Adler et al. |
| 8,059,160 B2 | 11/2011 | Shinozaki et al. |
| 8,089,509 B2 | 1/2012 | Chatenever et al. |
| 8,199,188 B2 | 6/2012 | Amling et al. |
| 8,274,559 B2 | 9/2012 | Amling et al. |
| 2004/0028390 A9 | 2/2004 | Chatenever et al. |
| 2006/0152516 A1 | 7/2006 | Plummer |
| 2007/0024717 A1 | 2/2007 | Chatenever et al. |
| 2007/0167814 A1 * | 7/2007 | Wakabayashi ............ A61B 8/12 600/459 |
| 2007/0188603 A1 * | 8/2007 | Riederer ................ G02B 21/22 348/54 |
| 2010/0295870 A1 | 11/2010 | Baghdadi et al. |
| 2011/0029733 A1 | 2/2011 | Adler et al. |
| 2012/0013755 A1 | 1/2012 | Shinozaki et al. |
| 2012/0082390 A1 * | 4/2012 | Kawasaki .......... A61B 1/00016 382/232 |
| 2013/0041226 A1 * | 2/2013 | McDowall ......... A61B 1/00009 600/166 |

OTHER PUBLICATIONS

U.S. Office Action U.S. Appl. No. 13/731,395 dated May 22, 2017 pp. 17.

* cited by examiner

CAMERA CONTROL UNIT WITH STEREOSCOPIC VIDEO RECORDING AND ARCHIVE

FIELD OF THE INVENTION

The invention relates to a modular medical imaging system having a control module connectable to a variety of input modules and, more particularly to a modular system where the control module provides general functions such as a user interface and general image processing that are not camera/source specific. The invention includes input modules that are capable of processing 3D image data from many different sources and converting the 3D image data into a format compatible with the control module.

BACKGROUND OF THE INVENTION

The field of endoscopy includes medical diagnostic and therapeutic disciplines that utilize endoscopes to view otherwise inaccessible locations in the body using minimally invasive surgical procedures. Endoscopes typically include a small, light-weight camera located at the distal tip of the endoscope to capture images.

In known systems, endoscopic cameras are typically connected to a Camera Control Unit ("CCU"), with the CCU processing and displaying the imaging data transmitted from the endoscopic camera. Often, different medical procedures require different types of cameras, which leads to a relatively large inventory of cameras. Additionally, each type of camera must be compatible with the CCU to function correctly. As such, the CCU is typically provided with software to process and operate a variety of different camera technologies, and as new technologies become available, the CCU may be updated to properly process images from the new camera. Additionally, often the CCU hardware becomes outdated, thus requiring an entirely new CCU to process the images of both old and new camera technologies used by a physician.

CCUs may be designed to be reprogrammable and reconfigurable, and as such, an older model CCU may sometimes be upgraded or configured to work with a new camera technology. However, in many cases the older model CCU may be too outdated to update or it may be less costly to replace the older model CCU with a new one because the reconfiguring of the CCU is often a time and labor intensive process that requires the CCU be returned to the manufacturer for disassembly, installation of new components, and testing. Moreover, while it may be possible to update software in older model CCUs, the existing hardware in older model CCUs may not allow for the older model CCUs to support software for newer technology image sensors and image formats provided with newly developed camera technology.

In known systems, endoscopic cameras used during endoscopic surgery are typically referred to as camera heads. To achieve the desired size and weight of the camera heads, camera head and/or integrated endoscope-camera assembly electronics are typically separated physically from the majority of circuitry required to process and output high-quality, color video images. Electronics for converting a "raw" or "unprocessed" video signal to a displayable format are typically housed in the CCU. In known systems, CCUs may be placed on or in carts, in or on ceiling boom arms, or may be permanently wall-mounted.

In known video imaging systems, a cable may connect a camera head to a CCU. When image data is acquired, or picked up, it is sent by the camera head to the CCU through the cable. Upon receiving the image data from the camera head, the CCU processes the signal and displays the acquired image on a viewing device. Generally, the image is used by a medical professional and/or for storage on various media (i.e., video cassette recorder, floppy disk, hard drives, flash drives, compact disks, digital video disks, and the like) and/or for transmission to remote locations in various manners, such as by the Intranet, Internet, radio transmission, and the like.

The CCU may also send commands to the camera head to adjust various settings on the camera head (i.e. color balance, electronic shutter for light sensitivity, and other optical and electronic characteristics).

Traditionally, CCUs are compatible with a limited number of camera heads. A CCU's hardware is usually difficult to configure for proper communication with varying types of camera heads because camera heads use varying types of imaging devices that can differ in pixel resolution, timing requirements (i.e. PAL, NTSC, Progressive, and other formats), signal output type (i.e. analog or digital), physical size, and in other characteristics. This is particularly the case for stereoscopic (3D) cameras.

Analog video system types differ in scanning principles, resolution capability, sampling rates, aspect ratios, synchronization, bandwidth, and the like. Moreover, video system types may differ between broadcast, closed circuit, and computer applications. Analog video systems are typically classified as either composite (luminance and chrominance components multiplexed into a single signal) or component (separate signals for each chrominance component, and synchronization signals). In broadcasting applications, composite formats are generally used. For closed circuit systems (such as video production and editing, medical, industrial, and scientific applications) component formats are typically used. The primary composite analog video standards used are PAL, NTSC, and SECAM, with one specific standard used in different geographical areas.

Digital video systems are typically differentiated by their application. Advanced television (ATV), high definition television (HDTV), and computer systems may differ in format and signal characteristics. In some areas, digital video formats and standards are currently being developed and adopted. The Society of Motion Picture and Television Engineers (SMPTE) normally defines and adopts voluminous digital video formal standards. As each is adopted, various applications, and application improvements generally are realized. Some digital video standards currently in use are: IEEE-1394 FireWire®, ISO/IEC IS 13818, International Standard (1994), MPEG-2, and ITU-R BT.601-4 (1994) Encoding Parameters of Digital Television for Studios.

Furthermore, there may be variability from device to device of the same type, which may affect camera head performance. Additionally, commands sent from the CCU to the camera head are generally unique depending upon the camera head type being used. Moreover, as repairs, modifications, or improvements are made to camera heads, the CCU, which was originally designed to be compatible with the older camera head, may become incompatible and may require upgrading as well.

3D camera heads utilize stereoscopic imaging, which typically comprises two imaging devices (e.g., a right imager and a left imager) where the digital image streams from the two imaging devices are combined into a single 3D image stream. In function, the right and the left imagers each generate data line-by-line, which is combined or interleaved and then sent to the CCU as a single data stream. When the image data of the two image streams is interleaved, every other line from each of the right and left imagers of the image streams are interleaved. This results in a loss of resolution, as the interleaved data stream sent to the CCU still requires the same bandwidth as is produced by a single imager. While through the interleaving process only every other line from each imager is used, the combined 3D image stream still sends the same amount of data (e.g., the combined data from each imager) to the CCU as is produced by a single imager, albeit at a lower resolution. The processing power for interleaving the two image streams requires a camera head that has increased size and/or weight to satisfy the power consumption required to interleave the two image streams. The variability of these factors can be dramatic depending on the type of the stereoscopic cameras used.

Furthermore, existing systems exhibit 3D image degradation that includes an increase in stereoscopic image crosstalk, increase in color bleed between the left and right images, decreased image contrast and loss of image structural detail.

This overall variability in camera heads, either caused by imaging device technologies or by CCU command characteristics, often results in a CCU being specifically designed to be compatible with a specific camera head type. Also, consumers may desire different capabilities related to specific applications of the cameras, such as medical, industrial, and scientific uses. Such desired system capabilities include picture in picture (PIP), reverse video (image flip), electronic zoom, electronic rotation, still image capture, and stereoscopic video interface.

Moreover, CCUs are typically designed for use with camera head technologies currently in existence, and are not designed to anticipate and accommodate camera heads yet to be developed. Hence, CCUs are typically not designed to be compatible with future camera head technologies; particularly, image device, image signal transmission technologies and 3D technologies. These differences between older and newer camera heads also contribute to compatibility problems.

Because CCUs are usually compatible with limited quantities of camera heads, CCUs are typically discarded in favor of ones that were designed concurrently and/or to be compatible with particular camera head technologies. Consequently, CCUs have become an added expense often associated with changing imaging devices or camera heads.

It is typically desired for camera heads to be improved due to the demand from consumers to have the latest technology and advancements in equipment. Moreover, CCUs used in medical and veterinary fields are increasingly being mounted permanently in equipment bays or carts and/or permanently mounted within the walls of surgical operating rooms themselves. The expense associated with replacing these existing CCUs to maintain compatibility with camera heads is subsequently passed onto consumers.

Thus, there exists a need for a modular imaging system that overcomes the disadvantages of the prior art. There exists a need to provide a system having a control module connectable to multiple input modules that may be connected to various camera heads and that may receive data in various formats from various camera heads. There exists a need for the input module to be connected to a control module, the input module and control module able to be updated or reprogrammed in an efficient and cost effective manner, rather than replacing the older input module or control module with a newer module. There exists a need for the modular imaging system, including at least one input module and a control module, to be readily compatible with existing and future imaging technologies and that allows for the at least one input module and the control module to be backwards and forwards compatible.

It is also desired to configure and control features of one module from another module upon attachment of one module to another via the cable. It is also desired to control the power state of one module via the other module upon attachment of the modules via the cable.

SUMMARY OF THE INVENTION

Accordingly, it is an object of the invention to provide a modular imaging system where the image acquisition, processing, control and display chain is segmented in such a manner as to optimize adaptability and compatibility with existing and yet to be developed image sensor formats and architectures, as well as with existing and yet to be developed display technologies.

It is also an object of the invention to support increasing varieties and sub-varieties of image sensors, which require unique interfaces for compatibility with video and display signal technologies.

These and other objects of the present invention are achieved by providing a modular imaging system having a control module, a first input module connectable to the control module and a second input module connectable to the control module. The first input module configured for receiving a first type image data and processing the first type image data into processed image data and the second input module configured for receiving a second type image data and processing the second type image data into processed image data. The control module configured for receiving the processed image data from the first and second input module.

In certain embodiments, the modular imaging system may further have a third input module configured for receiving a third type image data and processing the third type image data into processed image data for transmission to the control module.

The modular imaging system may further have a fourth input module configured for receiving a fourth type image data and processing the fourth type image data into processed image data for transmission to the control module.

The types of image data between the different modules may be differentiated by aspect ratio, timing, pixel rate, pixel resolution, and pixel encoding. The types of image data may also be differentiated by being analog, digital, standard definition, high definition or a combination thereof.

The control module may be used to further manipulate the processed image data into manipulated image data to provide zoom, PIP, graphical user interface (GUI), GUI overlay on an image, printing, video and still recording, and the like. A user may also annotate the image data by drawing or typing.

The control module may be connected to a display to display the manipulated image data and/or the processed image data. The control module may also output the manipulated image data and/or the processed image data to a hard drive, a personal computer, a printer, and the like.

A camera may be connected to the input module for transmitting image data, and a display can be connected to the control module for displaying processed and manipulated image data. The input module can receive and process still image data and video image data from a camera head.

The input module may receive and process digital video data. The digital video data may be sent in run-time programmable images sizes, color spaces, bit-depths and framerates.

The input module may receive and processes analog video data. The analog video data may be sent in run-time programmable images sizes, color spaces, bit-depths and framerates.

The input modules may be connected to the control module via cables or wirelessly. Still further, the cameras may be connected to the input modules via cables or wirelessly.

For 3D systems, stereoscopic imagers are utilized. This would entail use of a right imager and a left imager that are essentially aligned (e.g., within one or two pixels). In one embodiment, the two imagers can be mounted to the distal end of the endoscope shaft where each imager generates an image stream that is transmitted to the electronics in the body of the endoscope. It is contemplated that both of the two separate image streams are transmitted to the CCU for storage. This allows for all the acquired image data to be stored. The two image streams are then combined to form a 3D image stream, which is then transmitted to the display and may further be saved locally or remotely.

In one embodiment a video imaging system is provided comprising an endoscope having a shaft and/or a body portion, a camera control unit coupled to the endoscope, and a display coupled to the camera control unit. The endoscope has a first imager generating a first image stream and a second imager generating a second image stream. The first image stream is transmitted to the camera control unit and saved in a storage located in the camera control unit, and the second image stream is transmitted to the camera control unit and saved in the storage. The system also comprises a processor located in the camera control unit for processing the first image stream and the second image stream. The processor processes the first image stream and the second image stream into a 3D image stream that is presented on the display.

In certain embodiments, the storage location located in the camera control unit is a memory.

In certain embodiments, the first image stream comprises first lines of data from a first sensor and the second image stream comprises second lines of data from a second sensor, wherein the 3D image stream comprises alternating lines of data taken from the first image stream and the second image stream.

In certain embodiments, the 3D image stream is saved in the storage of the camera control unit.

In certain embodiments, the 3D image stream is saved on a removable storage.

In certain embodiments, the 3D image stream is encoded.

In certain embodiments, the 3D image stream is compressed prior to being saved in the storage.

In certain embodiments, the encoding is in a Top and Bottom (TaB) frame compatible format.

In certain embodiments, the encoding is in a Side-by-Side (SbS) frame compatible format or Alternating Line-by-Line (LbL) frame compatible format.

In certain embodiments, the encoding is MPEG-2 video coding or AVC/H.264 video coding.

In certain embodiments, the first and second imagers are positioned at a distal end of said shaft. In certain embodiments, the first and second sensors are positioned at a proximal end of the shaft.

In certain embodiments, the video imaging system further comprises a light source generating illuminating light.

In certain embodiments, said camera control unit further comprises a network connection.

In certain embodiments, the video imaging system further comprises a remote storage coupled to said network connection and the 3D image stream is stored on said remote storage via said network connection.

In certain embodiments, the video imaging system further comprises a remote computer and the first image stream and the second image stream are accessible by said remote computer via said network connection.

In another embodiment of the invention, a method for generating a 3D image is provided comprising the steps of generating a first image stream with a first imager positioned on an endoscope, generating a second image stream with a second imager positioned on the endoscope, and transmitting the first and the second image streams to a camera control unit coupled to the endoscope. The method further comprises the steps of storing the first and the second image streams on a storage in the camera control unit, processing the first image stream and the second image stream into a 3D image stream, and presenting the 3D image stream on a display coupled to the camera control unit.

In certain embodiments, the method further comprises the step of storing the 3D image stream in the storage.

In certain embodiments, the method further comprises the step of storing the 3D image stream in a removable storage.

In certain embodiments, the method further comprises the steps of transmitting the 3D image stream to a remote computer via a network connection and storing the 3D image stream on a remote storage.

In certain embodiments, the method further comprises the step of encoding the 3D image stream.

In certain embodiments, the method further comprises the step of compressing the 3D image stream.

In certain embodiments, the 3D image stream is generated by interleaving the first image stream and the second image stream using line-by-line interleaving.

In certain embodiments, the method further comprises de-interleaving the 3D image stream. In certain embodiments, the de-interleaving involves frame repacking into a Top half-of-frame (Right Image) half and Bottom half-of-frame (Left Image). In certain embodiments, the method further comprises passing the image to a H.264 encoder.

In certain embodiments, the method is used to perform stereosocopic 3D video H.264 encoding. In certain embodiments, the method is used with H.264 video encoders in existing hardware systems.

In another embodiment of the invention, a video imaging system is provided comprising: an endoscope having a shaft; a camera control unit coupled to said endoscope; a display coupled to said camera control unit; a first imager positioned on or within the endoscope shaft, the first imager generating a first image stream transmitted to said camera control unit and saved in a storage located in said camera control unit, said first image stream comprising first lines of data from a first sensor; a second imager positioned on or within the endoscope shaft, the second imager generating a second image stream transmitted to said camera control unit and saved in the storage, said second image stream comprising second lines of data from a second sensor; and a processor located in said camera control unit for processing the first image stream and the second image stream into a 3D image stream, the 3D image steam being presented on said display, wherein the 3D image stream encoded, wherein the encoding is selected from a group consisting of Top and Bottom (TaB) frame compatible format, Side-by-Side (SbS) frame compatible format and Alternating Line-by-Line (LbL) frame compatible format.

In another embodiment, a modular video imaging system is provided comprising: a first image stream; a second image stream; a camera control unit, the camera control unit comprising a processor, a storage located within said camera control unit, wherein the first image stream is transmitted to said camera control unit and stored in the storage, wherein the second image stream is transmitted to said camera control unit and stored in the storage, wherein the processor interleaves the first image stream and the second image stream into a 3D image stream, the 3D image stream comprising alternating lines of data taken from the first image stream and the second image stream.

In certain embodiments, the first image stream is generated by a first input device and the second image stream is generated by a second input device.

In certain embodiments, the first input device is a first imager positioned on or within an endoscope shaft and the second input device is a second imager positioned on or within an endoscope shaft.

In certain embodiments, the 3D image stream encoded. In certain embodiments, the encoding is selected from a group consisting of Top and Bottom (TaB) frame compatible format, Side-by-Side (SbS) frame compatible format and Alternating Line-by-Line (LbL) frame compatible format.

In certain embodiments, the 3D image stream is de-interleaved after being the 3D image stream is interleaved by the line-by-line interleaving of the first image stream and the second image stream.

In certain embodiments, an additional image stream is provided, the additional image stream being interleaved with the first image stream and the second image stream.

In certain embodiments, the interleaving of the first, second and additional image stream occur in a succession, whereby the streams are rotated upon interleaving the streams.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1A:
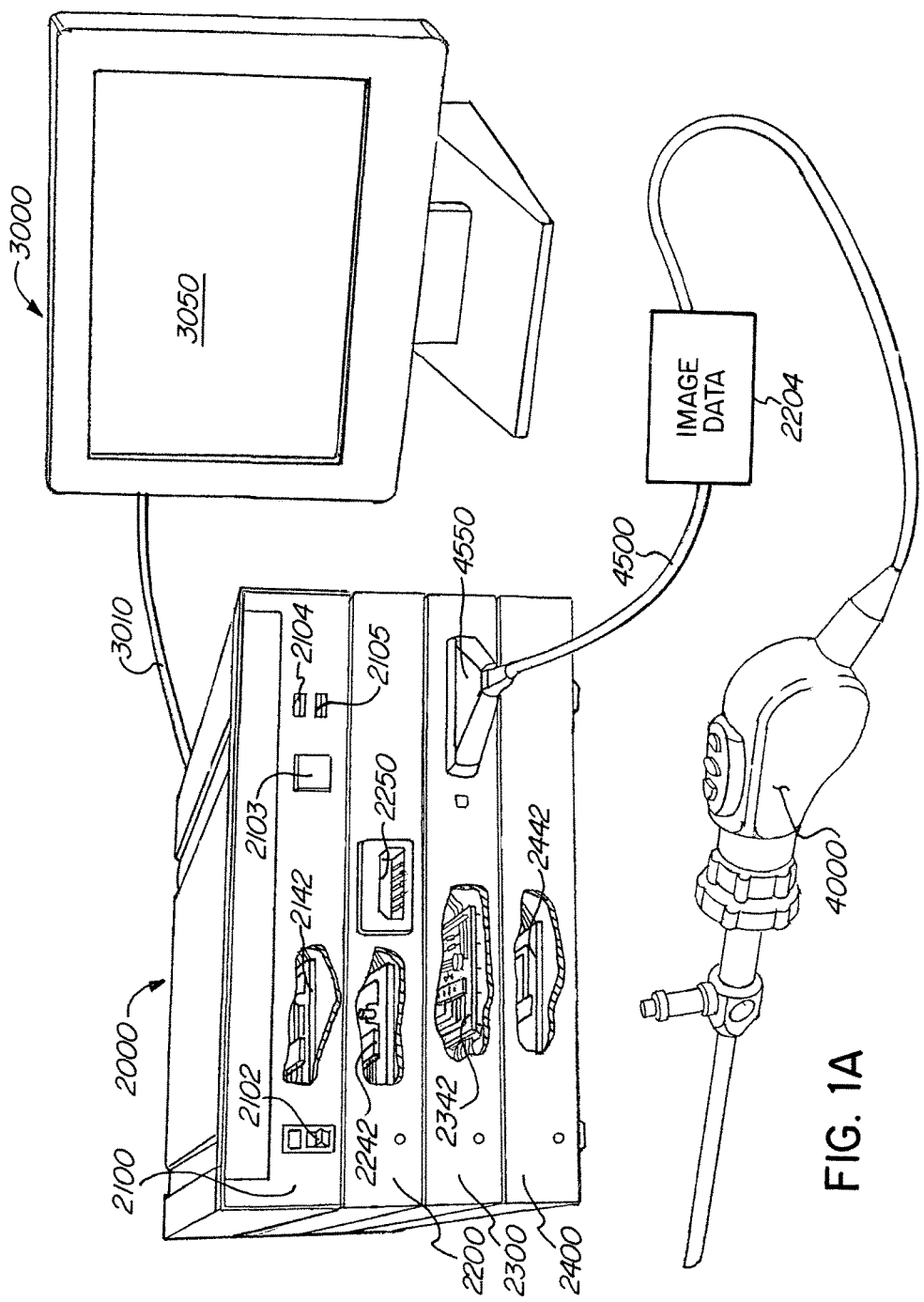
FIG. 1A is a perspective view of the front of an embodiment of the invention.

Accordingly, the invention involves a modular medical imaging system including several modules, such as an input module and a control module, which can be developed, sold and installed at different times. For example, a system may be initially installed with a control module and several input modules, and later additional modules can be added to the system.

According to one embodiment of the inventive video imaging system allows for later developed modules incorporating various technologies and industry standard interfaces as they evolve to be incorporated into an endoscopic system. By having modularity between the control module and input module, manufacturers can prevent having to re-design an entire new system for newer technologies and end users can avoid purchasing entirely new systems. The inventive video imaging system provides the ability to accommodate future imaging system improvements and adaptations as current technology limitations are overcome by adding new input modules, which are forward and backward compatible with the control module, without obsolescing initial customer investments in control modules. The system also provides the ability for a user to add a new control module to accommodate future improvements, which is forward and backward compatible with older input modules. This allows system users to take advantage of new features and functions of one module without requiring redesign and/or replacement of the entire system.

For example, industry standards in display and recording infrastructure technologies evolve at a different rate than, say, video endoscope technology, imaging technology, or proximal camera head technology. Newer technologies often use differing imaging data and parameters, such as aspect ratio, timing, pixel rate, pixel resolution, and pixel encoding. By having an input module connected to a control module, where the input module is forward and backward compatible with the control module, new camera technologies may be provided to replace outdated camera technologies, while still being compatible with older control modules.

Thus, a user can replace existing control modules with newer control modules that allow for a display having higher resolution, more color bit depth or being 3D compatible. Similarly, a user can replace an existing input module, which only supports a limited number of camera heads, without replacing the control module or the display.

Such a system provides a competitive advantage by being able to provide newer technologies faster and affords users the benefit of the backwards and forwards compatibility between the control modules and input modules.

The modular imaging system allows upgradeability and compatibility with a multitude of camera heads that are supported by a plurality of input modules, where the camera heads and input modules may be existing or are yet to be developed. Formerly, when a new imaging technology becomes available, a CCU would be incompatible with the new technology due to a variety of constraints, for example, outdated hardware. By using a modular architecture, the new technology is supported by a new input module that is backward compatible with the existing control module. The modular architecture increases the likelihood that existing visualization technology and yet to be developed visualization will be able to operate with some if not all of the same image processing hardware. This results in decreased capital costs for physicians' offices, surgical offices and/or hospitals.

In various embodiments of the invention, the control module may be designed to accommodate general image processing and display functions. These general functions include, for example, supporting a separate user interface, overlaying a user interface onto an image, image capture and streaming functionality as well as input/output functionality for the display/monitor interfaces, system interface and control, and network connectivity. The control module may be designed to accommodate a single input module or multiple input modules. The control module may be connected to a display or the control module may include a display as a one piece unit. The control module may include a processor as well.

For example, a user may only wish to purchase a control module and only one input module at a time. Thus, the overall modular system can be purchased at a lower initial cost. If the consumer wishes to purchase a new camera type, the modular system may be upgraded with a new input module to support the new imaging technology. The new input module may replace the old input module or be used together with the older input module.

The input modules may support functions required for a group or family of image sources, such as cameras or auxiliary inputs. The input module may provide compatibility between the family of image sources and the control module. Over the life of the system, additional input modules may be purchased to support emerging imaging technology such as 3D imaging, advanced fluorescence imaging, solid-state variable direction of view endoscopes, wireless camera heads and so on.

The group of input modules connected to the control module may include an auxiliary input module. The auxiliary input module may support a variety of video sources such as third party camera control units, C-Arm, X-Ray, Ultrasound, Personal Computers and the like. Supported input formats may include, DVI, VGA, S-Video, Composite, 3G-SDI and the like. Inputs may be both automatically and manually selected. The auxiliary module may provide increased backward compatibility, forward compatibility and third party image source compatibility.

It should be noted that as used herein, the categorization of Standard Definition (SD) or High Definition (HD) is not intended to limit the categories to a single signal format, but rather, many differing signal formats may be used. Furthermore, many different signal formats are categorized as SD and many different signal formats may be categorized as HD. For instance, SD generally refers to a line count of up to approximately 720×480 NTSC and PAL; while HD refers to systems that utilize a higher line count and may include, but is not limited to, 1280×720 progressive, 1920×1080 interlaced, or 1920×1080 progressive which are only three of the commonly used HD resolutions. HD resolution also includes 1080p or Full HD resolution.

In various embodiments, the modules are capable of sending digital video in the form of HD and SD video over the cable from module to module at fully run-time programmable image sizes, color spaces, bit-depths and frame-rates. The receiving and transmitting ends of the video signals can auto-negotiate these various parameters.

There are commonly used types of signal formats, however, and it is contemplated that additional formats may be provided for; especially new signal formats that may become available. Two commonly used SD format types are NTSC and PAL. It should be noted that these are just two video signal formats and that there are many differing types and modifications to the above-listed types including, for example, a modified version Phase-Alternating Line (PAL-M).

In addition to the standard NTSC and PAL SD (NTSC and PAL) composite, RGB, and s-video (Y/C) outputs, numerous other outputs may be used. The following examples are presented to further illustrate and explain the present invention and should not be taken as limiting in any regard.

Serial Digital Interface (SDI), standardized in ITU-R BT.656 and SMPTE 259M, is a digital video interface used for broadcast-grade video. A related standard, known as High Definition Serial Digital Interface (HD-SDI), is standardized in SMPTE 292M and provides a nominal data rate of 1.485 Gbit/s. Another standard is 3G-SDI. 3G-SDi provides a nominal data rate of 2.970 Gbit/s, and 2.970/1.001 Gbit/s and works with 1080p resolution.

Digital Visual Interface (DVI) is a video interface standard designed to maximize the visual quality of digital display devices such as flat panel LCD computer displays and digital projectors and is partially compatible with the HDMI standard in digital mode (DVI-D). The DVI interface uses a digital protocol in which the desired illumination of pixels is transmitted as binary data. When the display is driven at its native resolution, it will read each number and apply that brightness to the appropriate pixel. In this way, each pixel in the output buffer of the source device corresponds directly to one pixel in the display device.

High-Definition Multimedia Interface (HDMI) is an all-digital audio/visual interface capable of transmitting uncompressed streams. HDMI is compatible with High-bandwidth Digital Content Protection (HDCP) Digital Rights Management technology. HDMI provides an interface between any compatible digital audio/video source and a compatible digital audio and/or video monitor, such as a digital television (DTV).

The modular architecture of the present system allows buyers to progressively and economically upgrade their imaging technology, rather than being required to purchase a CCU that is compatible with the entire range of imagers that the buyer would wish to purchase in the future. The system allows for hardware upgrades through the modules as well as software feature upgrades. Further, the cost of ownership and upgrade, such as acquisition, back-up, and maintenance, is reduced.

Referring now to the drawings, wherein like reference numerals designate corresponding structure throughout the views.

FIG. 1A shows a perspective view of the endoscopic system including a camera control unit 2000 that comprises input modules 2200, 2300 and 2400, and the control module 2100 stacked upon one another. Control module 2100 is shown connected to display 3000. In certain embodiments, the control module 2100 may be separate from the display 3000 and in other embodiments the control module 2100 may form a one-piece unit with the display. In certain embodiments, the display has a screen 3050, which may be a touch screen.

Figure 1B:
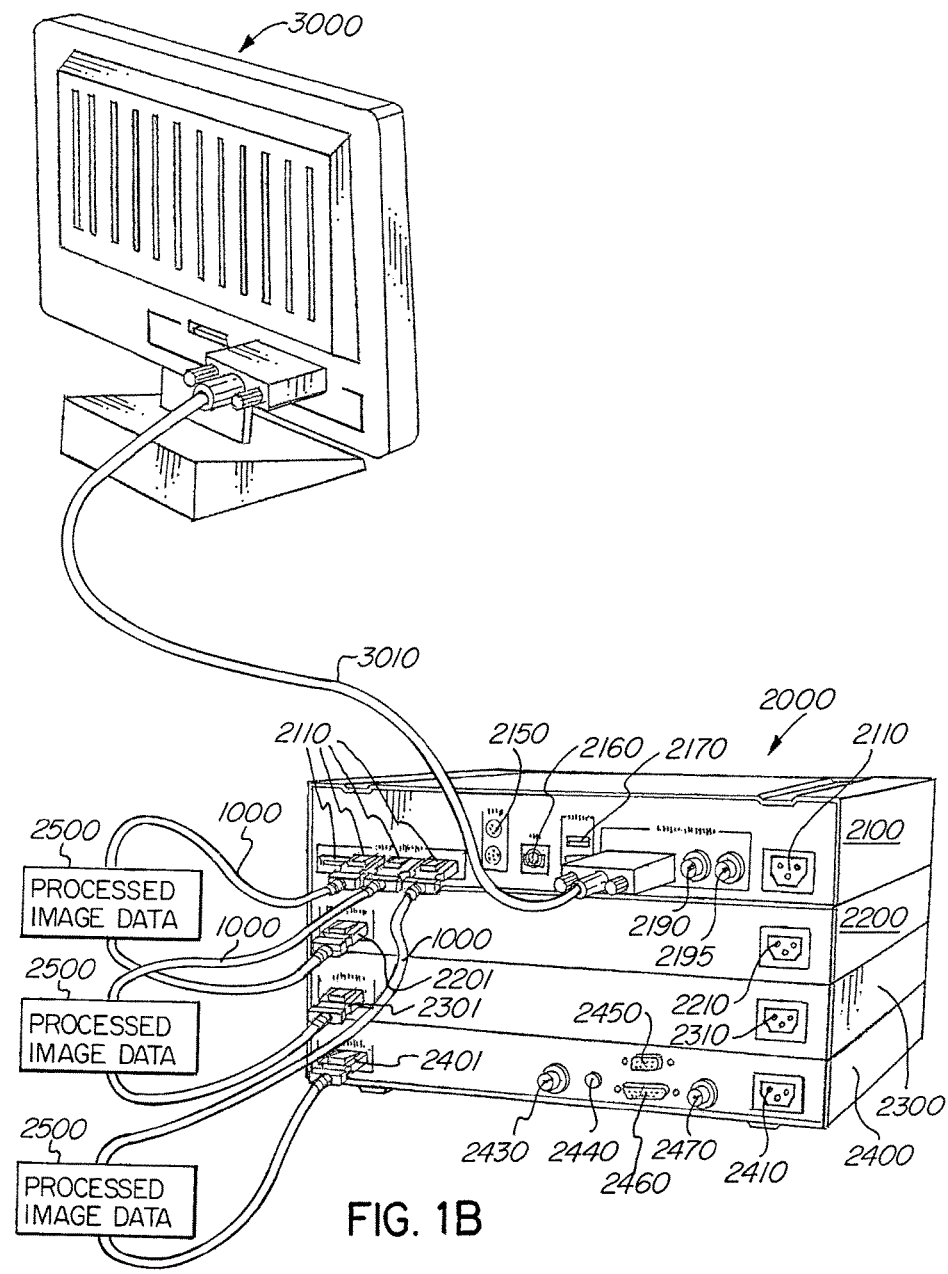
FIG. 1B is a rear perspective view of FIG. 1A.

Internal portions of input modules 2200, 2300 and 2400 are also shown in FIG. 1A. Input module 2300 is shown having a processor 2342 that converts image data 2204 received from the camera head 4000 into processed image data that is compatible with the control module 2100. Similarly, input module 2200 is shown having a processor 2242 and input module 2400 is shown having a processor 2442. The processor 2242 and 2442 convert image data received from differing camera heads into processed image data 2500 (ref. FIG. 1B) that is compatible with the control module 2100.

Input modules 2200, 2300, and 2400 may be configured to receive and process numerous types of image data 2204. Image data 2204 may include analog data such as CCD based video endoscopes (⅛", 1/10" CCDs) (Pre-CDS analog); CMOS; and/or 720p60 single chip Digital Proximal Heads (for smaller camera heads requiring less than 1080p resolution but better than Standard Definition (SD)). Image data 2204 may also be analog High Definition (HD) image data such as from 3-Chip HD CCD camera heads or digital HD image data such as from 1080p60 3chip camera heads (CMOS) or 1080p60 1chip camera heads (CMOS). Finally image data 2204 may also be advanced fluorescence imaging, solid-state variable direction of view endoscopes, wireless camera heads and so on.

The camera head 4000 is connected to input module 2300 by a cable 4500. Cable 4500 has a connector 4550 that connects into a slot such as shown in input module 2200 as slot 2250. Camera head 4000 may send image data 2204 to the input module through the cable 4500.

Control module 2100 is shown having an on/off switch 2102, which, in certain embodiments, can control the power of all of the input modules 2200, 2300 and 2400. Control module 2100 is also shown having input slots or ports 2104 and 2105 as well as a white balance control switch 2103.

FIG. 1B shows control module 2100 being connected to input modules 2200, 2300 and 2400 via cables 1000. FIG. 1B also shows display 3000 connected to control module 2100 via cable 3010.

FIG. 1B shows input modules 2200, 2300 and 2400 each having a power plug 2210, 2310 and 2410 respectively. Each input module may have one or more integral power supplies to support an ever increasing variety of camera heads and their unique power requirements. Control module 2100 is shown having four slots 2110 for receiving cables 1000. In certain embodiments, only three slots are provided and a fewer and greater amount of slots are contemplated in various embodiments of the invention. Control module 2100 also has various connection elements 2150, 2160, 2170, 2190 and 2195 to connect to various other devices including input and output devices. Such input/output devices may include printers, external storage devices, personal computers, local area networks, light sources, keyboards, and/or Accessory (ACC) port adapters. Other example input/output elements may include DVI output for DVI monitors or recorders, 3G SDI outputs for 3G SDI monitors or recorders Input modules 2200, 2300 and 2400 each have a slot 2201, 2301, 2401 respectively for receiving the cable 1000 which transfers information between the input modules and the control module 2100, such as processed image data 2500. Input module 2400 has various input and output elements 2430, 2440, 2450, 2460 and 2470 to connect to various other input and output devices. Such input/output devices may include existing or third-party CCUs, C-Arm, X-Ray, Ultrasound, and personal computers. Such inputs may also include DVI, VGA, S-Video, Composite, 3G-SDI. Other additional input and output elements may be envisioned for the various input modules 2200, 2300 and 2400.

Figure 2:
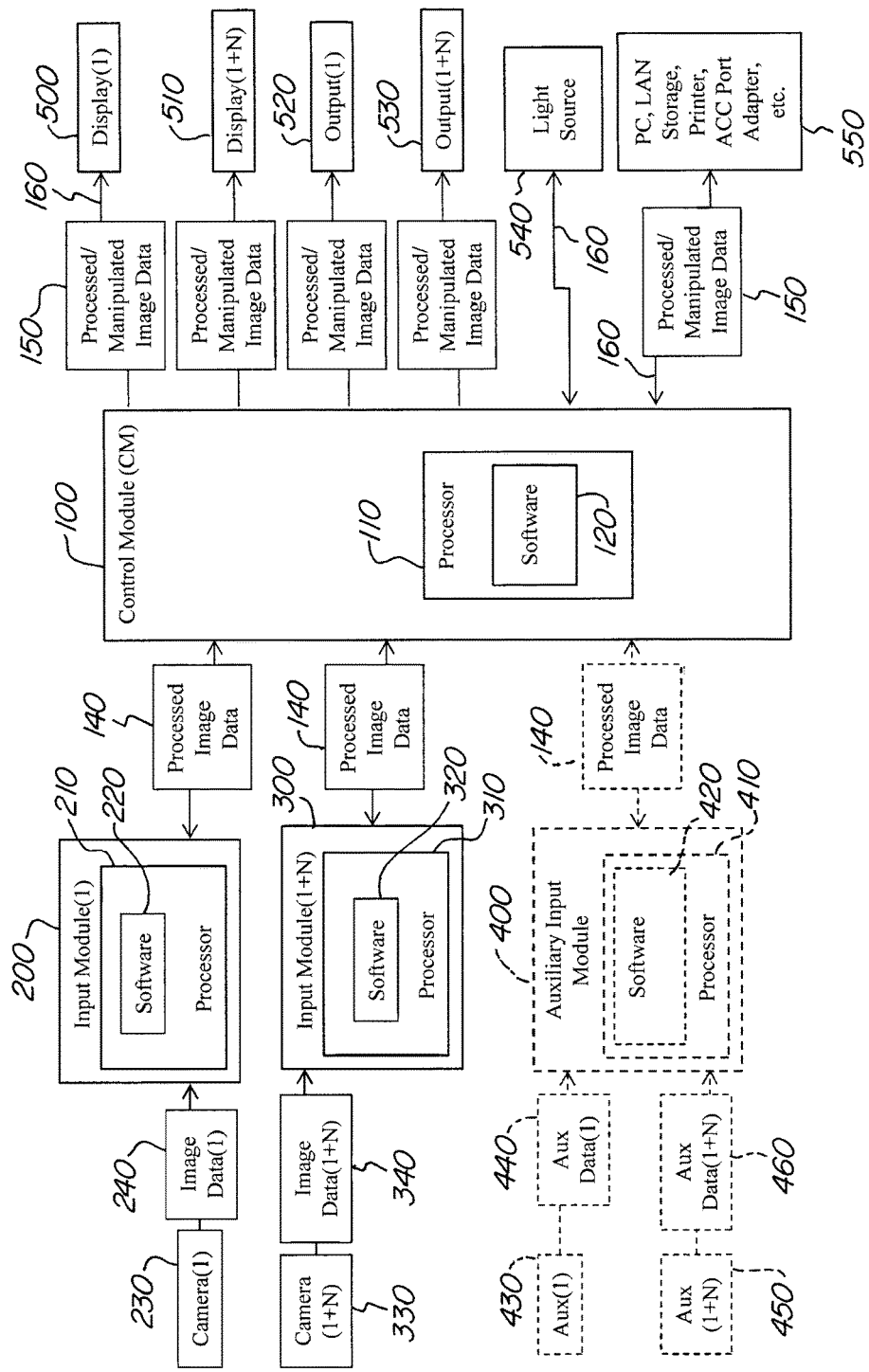
FIG. 2 is a block diagram according to FIGS. 1A and 1B.

FIG. 2 is a schematic of a modular medical imaging system that may be used, for example, in a hospital. The system has a control module 100 that can be connected to multiple input modules 200, 300, 400 that support different types of image data 240, 340, 440, 460 and process the image data 240, 340, 440, 460 into processed image data 140 which is a format compatible with the control module 100. The control module then handles functions not specific to the image data 240, 340, 440, 460 such as general image processing and outputs processed and/or manipulated image data 150 to a display/output 500, 510, 520, 530, 550.

More specifically, in this system camera(1) 230 and camera(1+N) 330 output different types of image data, image data(1) 240 and image data(1+N) 340 respectively. Therefore, input module(1) 200 receives image data(1) 240 and processes it into processed image data 140 to be sent to the control module 100. Camera(1+N) 330 is not compatible with input module(1) 200 so it is connected to input module (1+N) 300, which supports image data(1+N) 340. Input module(1+N) 300 receives image data(1+N) 340 and processes it into processed image data 140 to be sent to the control module 100.

It should be understood that input module 200, 300, 400 can be configured to receive multiple types of image data. Furthermore, image data may be for a single type of camera or a family of cameras. It should also be understood that the input modules may process the image data through hardware or software or some combination of hardware and software. For instance, input module(1) can implement a processor 210 running software 220 to process image data(1) 240 into processed image data 140. Similarly, input module(1+N) can implement a processor 310 running software 320 to process image data(1+N) 340 into processed image data 140.

The system may also implement an auxiliary input module 400, which can support multiple auxiliary devices. In this case, Aux(1) 430 outputs Aux Data(1) 440 that is received by the auxiliary input module 400 and processed into processed image data 140. Aux(1+N) 450 outputs aux data(1+N) 460 that is received by the auxiliary input module 400 and processed into processed image data 140. It should also be understood that the auxiliary input module 400 may process the image data through hardware or software or some combination of hardware and software. In one embodiment, auxiliary input module 400 can implement a processor 410 running software 420 to process image data 440, 460 into processed image data 140.

It should be understood that terms input module and auxiliary input module can be used interchangeably as the purpose of the input/auxiliary modules is to process differing types of image data into a standard format for the control module 100. It should also be understood that while FIG. 2 shows each input module 200, 300, 400 being connected to the control module 100 with a cable, that the input modules and control module 100 can be wirelessly connected.

Control module 100 receives processed image data 140 from either all or some of the input modules 200, 300, 400 and can carry out general image processing, user interface and connect with various outputs. For instance, the control module 100 can connect to a touch screen display which provides a user interface through which to control the module. The control module can further process the processed image data 140 and transmit the process/manipulated image data 150 to various places, such as displays 500, 510, outputs 520, 530, PCs, LANs, Storage devices, and printers, etc. The process/manipulated data 150 can be any combination of processed and/or manipulated data. Manipulation to the data can include overlaying a graphical user interface (GUI) on an image, zooming in on an image, and picture-in-picture of multiple sources including from other input modules. Manipulation to the data may also include image rotation, perspective correction, cropping, pan and scan, tilt and mirror in the horizontal and the vertical direction, and correcting for endoscope artifacts.

The control module 100 may also be configured to provide artificial horizon, wide angle lens support, adaptive camera perspective to surgeon perspective, intelligent image pan/scan controlled via surgeon movement.

It should be understood that the control module 100 may further process the image data 140 through hardware or software or some combination of hardware and software. For instance, control module 100 can implement a processor 110 running software 120 to further process the processed image data 140 into manipulated image data 150.

In order to be backwards and forwards compatible the control module 100 and input modules 200, 300, 400 may have to communicate what types of standard processed image data 140 they are compatible with. For instance, control module 100 may be compatible with several types of standard processed image data (e.g. HD or SD) and may have to communicate this compatibility with each input modules 200, 300, 400 in turn the input modules may have to communicate what types of standard processed image data 140 they are capable of transmitting. By communicating this information between the control module 100 and each input module 200, 300, 400 can settle on a type of standard processed image data 140 to communicate. Such functionality allows for the use of newer control modules with older input modules and newer input module with older control modules. For instance, if an input module was made for a newer imaging technology (e.g. HD) the input module may be capable of transmitting processed image data in HD or SD formats so that the new HD input module could function with an older SD control module. Likewise, if a user had a newer HD control module, the control module would be able to receive both HD and SD image data such that the HD control module would be backwards compatible with SD input modules.

In certain embodiments, the control module 100 is connected to, for example, an Intranet, the Internet and/or the like. In certain embodiments, the input modules 200, 300, 400 and/or the control module 100 includes WI-FI and/or a way to receive information directly from the Internet, either wired or wirelessly. In certain embodiments, any of the input modules may wirelessly connect to a related camera.

In certain embodiments, upon connection of control module 100 to, for example, input module 200 an input module identifier/program stored on input module 200 may be transmitted to the control module. It is contemplated that the input module identifier may comprise discrete data or may comprise a program that provides information relating to the input module 200 to the control module 100. In addition, it is contemplated that the control module 100 may also transmit a control module identifier/program stored on the control module 100 to the input module 200. It is contemplated that the control module identifier may comprise discrete data or may comprise a program that provides information relating to the control module 100 to the input module 200.

In certain embodiments, the control module 100 may send commands to the input module 200, which may include, for example, adjusting color balance, light, focal distance, resolution, zoom, focus, shading, and other optical characteristics if the input is a camera video or video endoscope. Input module 200 may then generate and transmit processed image data 140 to control module 100.

Figure 3:
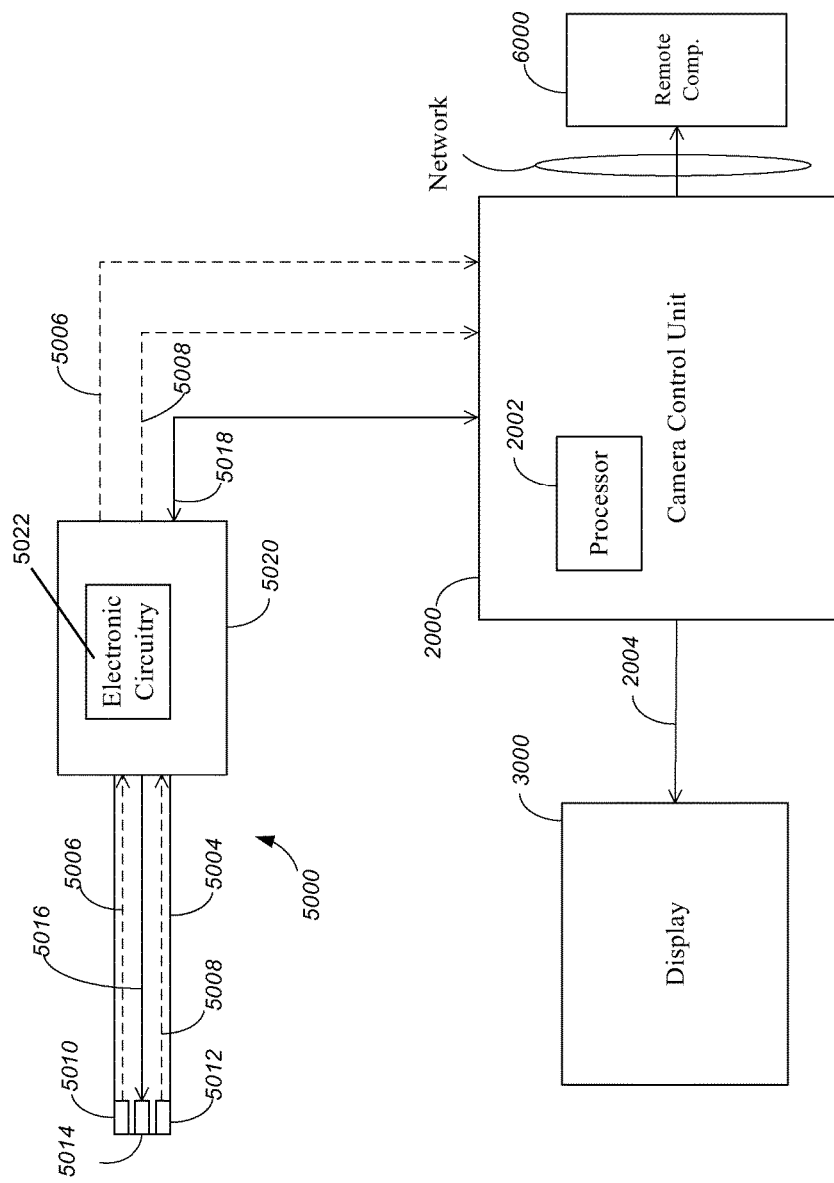
FIG. 3 is a block diagram according to FIGS. 1A and 1B.
Figure 4:
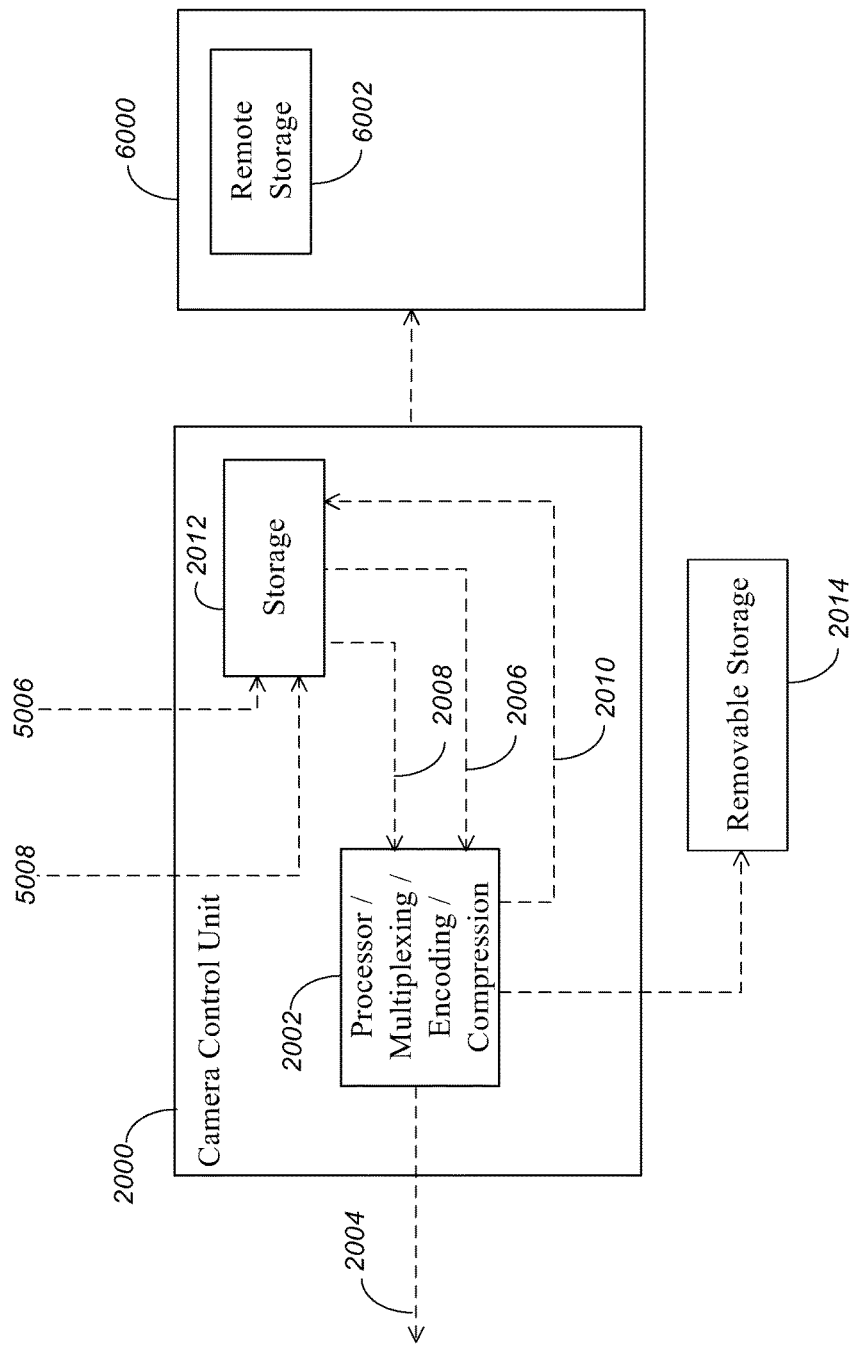
FIG. 4 is a block diagram according to FIG. 3.

Referring now to FIGS. 3 and 4, a schematic including an endoscope 5000 having a housing 5020 and a shaft 5004 are provided. The endoscope is connected to a camera control unit 2000 that may comprise multiple modules as previously described herein. The control unit 2000 is connected to a display 3000. Additionally, the control unit 2000 is connected to a remote computer 6000 via a network connection.

The shaft 5004 of endoscope 5000 may comprise either a rigid or flexible shaft or may comprise a combination of the two (e.g., the proximal end of the shaft 5004 coupled to the housing 5020 may comprise a rigid portion, while the distal end may comprise a flexible portion). Also shown in FIG. 3 is a first imager 5010 and a second imager 5012, which in the figure are depicted at a distal end of the shaft 5004. It is contemplated that the first and second imagers 5010, 5012 are provided as a stereoscopic imaging system where the first imager 5010 generates a first image stream 5006 and the second imager 5012 generates a second image stream 5008.

Both the first and second image streams 5006, 5008 are transmitted to the housing 5020 to be received by electronic circuitry 5022. In other embodiments, the first imager 5010 and a second imager 5012 are located within the shaft 5004 or may be located at the proximal end of the shaft 5004.

The first and second image streams 5006, 5008 are further transmitted to the control unit 2000 for processing as indicated in FIG. 3. The electronic circuitry 5022 may comprise any number of different electronic circuits, but in one embodiment may provide pre-processing of the image stream(s) including, for example, amplification prior to transmission to the control unit 2000.

Also shown at the distal end of the shaft 5004 is a light source 5014, which may comprise, for example, an LED that receives power via a line 5016. Illuminating light from the light source 5014 impinges on the area to be viewed and reflected light is then picked up by first and second imagers 5010, 5012 which generate corresponding first and second image streams 5006, 5008. Alternatively, it is contemplated that the light source 5014 may be positioned in the housing 5020 and the illuminating light is transmitted down the shaft via fiber optic cables to illuminate the area to be viewed. Still further, the light source could further be positioned in the control unit 2000 and the illuminating light could be transmitted from the control unit 2000 via fiber optic cables through the shaft 5004 to illuminate the area to be viewed. In the latter embodiment, the illuminating light could travel through the housing 5020 or a light cable extending from the control unit 2000 could couple directly to the shaft 5004 (e.g., a lateral connection). In other embodiments, an external light source (not shown) may be provided. In other embodiments, the external light source is directly coupled to shaft 5004 or to housing 5020.

Line 5018 is provided to illustrate that various information and/or energy is transmitted between the endoscope 5000 and the control unit 2000. For example, various command and control information may be transmitted down line 5018 including identification information from the endoscope 5000 to the control unit 2000 allowing the control unit 2000 to configure itself to function with the particular type of endoscope attached. Likewise, various command data may be transmitted to the endoscope to facilitate the proper functioning of the endoscope 2000. Line 5018 may also be used to provide power to endoscope 5000, and electronic circuitry 5022 may include a battery (not shown) that charges up to provide uninterrupted power to endoscope 5000. Additionally, while various lines (5006, 5008, 5018) are shown in FIG. 3, it will be understood that a wireless connection between the endoscope 5000 and the control unit 2000 may be utilized.

Turning now to the control unit 2000, it should be understood that any configuration as previously discussed herein is applicable to the control unit of FIGS. 3 and 4, including the control unit 2000 comprising multiple modular units. A processor 2002 is included in FIG. 3, which is provided for processing of the first and second image streams 5006, 5008.

Referring to FIG. 4, which shows the control unit 2000 in greater detail, the processor 2002 and storage 2012 are shown inside control unit 2000. The first and second image streams 5006, 5008 are depicted as entering the control unit and into the storage 2012, where both of the image streams are stored. It will be understood that the image streams may also be simultaneously sent to both the processor 2002 and the storage 2012. Both the first and second image streams 5006, 5008 are saved on the storage. The first and second image streams 5006, 5008 are also sent to the processor where they are processed into a 3D image stream. The 3D image stream is then transmitted to display 3000 via a line 2004, which may be a cable or a wireless connection.

The 3D image stream is a composite of the first and second image streams 5006, 5008. The Image stream 2204 is comprised of lines of data where every other line of data from the first and second image streams 5006, 5008 are combined (interleaved) to generate the 3D image stream.

In certain embodiments, the 3D image stream is formatted in a line-by-line interleave format using AVC/H.264 Video coding.

There are various forms of multiplexing that can be used to generate the 3D image stream such as Top and Bottom (TaB) frame compatible format multiplexing. TaB formatting must be used with progressive (720p and 1080p) HD video formats and may be used with MPEG-2 or with AVC/H.264 Video coding. TaB formatting must also be oriented with the Left-eye image on the top half of the frame and Right-eye image on the bottom half of the frame, without any inversion or mirroring. For 720p formats, the Left-eye image occupies lines 26 to 385, and the Right-eye image occupies lines 386 to 745, for example. For 1080p formats, the Left-eye image occupies lines 42 to 581, and the Right-eye image occupies lines 582 to 1121. TaB formatting is coded using any anti-aliased resizing algorithm that reduces resolution and alias components only in the vertical direction without specific line structure orientation between left and right views. This means that a simple 2-dimensional image processed in this way will produce exactly the same reduced image for the left and right views.

In certain embodiments, such a TaB frame multiplexing involves de-interleaving the 3D image frame and repacking it into a Top half-of-frame (Right Image) and Bottom half-of-frame (Left Image) before passing the image to a display. In certain embodiments, the de-interleaving the 3D image is done before passing the image to standard H.264 encoders. In certain embodiments, this is done without using Multiview Video Coding (MVC) features of H.264 encoders. In certain embodiments the viewed playback of an H.264 recording is performed on a commercial 3D display that supports 3D Top/Bottom display modes.

In certain embodiments, various forms of multiplexing involves data that is saved to storage and also data that is sent to a display. Moreover, if the system has a high bandwidth, then the data could be sent directly to a display in certain embodiments.

Another form of multiplexing that can be used to generate the 3D image stream is Side-by-Side (SbS) frame compatible format. SbS formatting may be used with interlaced HD video formats, such as 1080i or 1080p. SbS formatting may be used with MPEG-2 or with AVC/H.264 Video coding. SbS formatting is oriented with the Left-eye image on the left half of the frame and Right-eye image on the right half of the frame, without any inversion or mirroring. SbS formatting is also coded using any anti-aliased resizing algorithm that reduces resolution and alias components only in the horizontal direction without specific column structure orientation between left and right views. This means that a simple 2-dimensional image processed in this way will produce exactly the same reduced image for the left and right views.

Another form of multiplexing that can be used to generate the 3D image stream is Alternating Line-by-Line interleave (LbL). Alternating Line-by-Line interleave involves alternating lines from the first and second image streams into a 3D image stream.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A video imaging system comprising:
   an endoscope having a shaft;
   a camera control unit including an input module and a control module disposed external to the input module, the control module being coupled to the input module and the input module being coupled to said endoscope;
   a first imager positioned on or within the endoscope, the first imager generating a first image stream transmitted to said input module, said first image stream comprising first lines of data from a first sensor;
   a second imager positioned on or within the endoscope, the second imager generating a second image stream transmitted to said input module, said second image stream comprising second lines of data from a second sensor;
   the input module supporting functions of the first imager and the second imager and being configured to process the first image stream and the second image stream into a first processed image stream and a second processed image stream; and
   a processor located in said control module for processing the first processed image stream and the second processed image stream into a 3D image stream, the 3D image stream being transmitted to a display to be presented on said display;
   wherein the 3D image stream comprises alternating lines of data taken from the first processed image stream and the second processed image stream;
   wherein, upon connection of the input module to the control module, said control module is configured to communicate to the input module a plurality of types of standard processed image data the control module is compatible with, and said input module is configured to communicate to said control module a plurality of types of standard processed image data the input module is configured to transmit; and
   wherein said control module and said input module are configured to, by said communicating, settle on a type of standard processed image data to transmit.

2. The video imaging system of claim 1 wherein the 3D image stream is saved in the storage of the camera control unit.

3. The video imaging system of claim 1 wherein the 3D image stream is saved on a removable storage.

4. The video imaging system of claim 1 wherein the 3D image stream is encoded.

5. The video imaging system of claim 4 wherein the 3D image stream is compressed prior to being saved in the storage.

6. The video imaging system of claim 4 wherein the encoding is Top and Bottom (TaB) frame compatible format.

7. The video imaging system of claim 4 wherein the encoding is Side-by-Side (SbS) frame compatible format or Alternating Line-by-Line (LbL) frame compatible format.

8. The video imaging system of claim 4 wherein the encoding is MPEG-2 video coding or AVC/H.264 video coding.

9. The video imaging system of claim 1 wherein the first and second imagers are positioned at a distal end of said shaft.

10. The video imaging system of claim 1 further comprising a light source generating illuminating light.

11. The video imaging system of claim 1 wherein said camera control unit further comprises a network connection.

12. The video imaging system of claim 11 further comprising a remote storage coupled to said network connection and the 3D image stream is stored on said remote storage.

13. The video imaging system of claim 11 further comprising a remote computer and the first image stream and the second image stream are accessible by said remote computer via said network connection.

14. The video imaging system of claim 1 wherein the 3D image stream is processed from the first image stream and the second image stream that are saved in the storage.

15. A method for generating a 3D image comprising the steps of:
generating a first image stream with a first imager positioned on or within an endoscope;
generating a second image stream with a second imager positioned on or within the endoscope;
transmitting the first and the second image streams to an input module coupled to the endoscope;
processing, via the input module, the first image stream and the second image stream into a first processed image stream and a second processed image stream;
transmitting the first and second processed image streams to a control module, the control module being disposed external to the input module and coupled to the input module;
processing the first processed image stream and the second processed image stream into a 3D image stream, the 3D image stream comprising alternating lines of data taken from the first processed image stream and the second processed image stream; and
transmitting the 3D image stream to a display coupled to the control module for displaying the 3D image stream;
wherein, upon connection of the input module to the control module, said control module is configured to communicate to the input module a plurality of types of standard processed image data the control module is compatible with, and said input module is configured to communicate to said control module a plurality of types of standard processed image data the input module is configured to transmit; and
wherein said control module and said input module are configured to, by said communicating, settle on a type of standard processed image data to transmit.

16. The method of claim 15 further comprising the step of storing the 3D image stream in the storage.

17. The method of claim 16 further comprising the steps of transmitting the 3D image stream to a remote computer via a network connection and storing the 3D image stream on a remote storage.

18. The method of claim 15 further comprising the step of storing the 3D image stream in a removable storage.

19. The method of claim 15 further comprising the step of encoding the 3D image stream.

20. The method of claim 15 further comprising the step of compressing the 3D image stream.

21. A video imaging system comprising:
an endoscope having a shaft;
a camera control unit including an input module and a control module disposed external to the input module, the control module being coupled to the input module and the input module being coupled to said endoscope;
a first imager positioned on or within the endoscope, the first imager generating a first image stream transmitted to said input module, said first image stream comprising first lines of data from a first sensor;
a second imager positioned on or within the endoscope, the second imager generating a second image stream transmitted to said input module, said second image stream comprising second lines of data from a second sensor;
the input module transmitting an input module identifier to the control module, the input module being configured to process the first image stream and the second image stream based on a command to generate a first processed image stream and a second processed image stream; and
the control module being configured to determine the command based on the input module identifier and user input and transmit the command to the input module, the control module having a processor for processing the first processed image stream and the second processed image stream into a 3D image stream, the 3D image stream being transmitted to a display to be presented on said display;
wherein the 3D image stream is encoded, wherein the encoding is selected from a group consisting of Top and Bottom (TaB) frame compatible format, Side-by-Side (SbS) frame compatible format and Alternating Line-by-Line (LbL) frame compatible format.

22. A modular video imaging system comprising:
a first image stream;
a second image stream;
a camera control unit, the camera control unit comprising:
an input module configured to process the first image stream and the second image stream into a first processed image stream and a second processed image stream;
a control module disposed external to the input module and coupled to the input module, the control module having a processor; and
a storage located within said camera control unit;
wherein the first processed image stream is transmitted to said control module and stored in the storage;
wherein the second processed image stream is transmitted to said control module and stored in the storage;
wherein the processor interleaves the first processed image stream and the second processed image stream into a 3D image stream, the 3D image stream comprising alternating lines of data taken from the first processed image stream and the second processed image stream, and wherein the 3D image stream is transmitted to a display;
wherein, upon connection of the input module to the control module, said control module is configured to communicate to the input module a plurality of types of standard processed image data the control module is compatible with, and said input module is configured to communicate to said control module a plurality of types of standard processed image data the input module is configured to transmit; and
wherein said control module and said input module are configured to, by said communicating, settle on a type of standard processed image data to transmit.

* * * * *